United States Patent [19]

Pintschovius

[11] 4,154,951
[45] May 15, 1979

[54] BIS-NAPHTHYL-ETHYLENES

[75] Inventor: Ulrich Pintschovius, Hattersheim, Fed. Rep. of Germany

[73] Assignee: Hoechst Aktiengesellschaft, Frankfurt am Main, Fed. Rep. of Germany

[21] Appl. No.: 532,910

[22] Filed: Dec. 16, 1974

[30] Foreign Application Priority Data

Dec. 20, 1973 [DE] Fed. Rep. of Germany ....... 2363416

[51] Int. Cl.² ..................... C07C 63/60; C07C 69/76; C07C 121/60
[52] U.S. Cl. ..................................... 560/80; 8/1 W; 252/301.21; 260/465 D; 260/465 H; 427/158; 562/488
[58] Field of Search ........ 260/475 FR, 465 D, 465 H; 560/80; 562/488

[56] References Cited

U.S. PATENT DOCUMENTS 3,822,305   7/1974   Pintschovius et al. .............. 260/465

Primary Examiner—Dolph H. Torrence
Attorney, Agent, or Firm—Connolly and Hutz

[57] ABSTRACT

A compound of the formula (1)

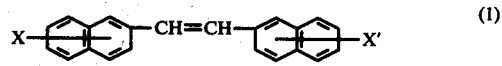

in which X and X' stand for an optionally functionally modified carboxy or sulfo group and wherein the naphthalene nuclei may carry further non-chromophoric substituents and a process for their preparation. These compounds are valuable optical brighteners and can be applied by the methods known in this field.

2 Claims, No Drawings

BIS-NAPHTHYL-ETHYLENES

Substituted 1-(mono-styryl)-napthalene compounds which are colorless to weakly yellow dyed and form in solution a violettish-blue to greenish-blue fluorescence as well as their utilization as optical brighteners are known from the German Pat. No. 2,060,228.

The present invention concerns colorless to weakly yellow bis-naphthyle-(2)-ethylene derivatives which correspond to the formula (1) below and which fluoresce between 410 and 450 mm

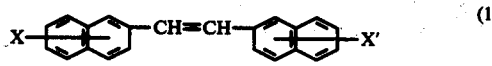 (1)

In this formula X and X', which may be identical or different, stand for a COOMe group, in which Me stands for hydrogen or a colorless cation, for a functional derivative of the carboxy group such as, a cyano- or carboxylic acid amide group, which may have on the carboxylic acid amide-nitrogen further substituents, a carboxylic acid ester group, which derives from lower or eventually from substituted alcohols or phenols, an $SO_3Me$ group, whereby Me has the above meaning, or a functional derivative of a sulfo group such as, sulfonamido-, sulfonic acid alkyl- or aryl ester group or a lower alkyl sulfonyl radical, in which the alkyl radical may be eventually again be substituted.

Onto the naphthalene nuclei further non-chromophoric substituents may be bound such as alkyl, alkenyl or alkoxy groups with 1–6 carbon atoms, phenyl groups or functional derivatives of carboxy- or sulfo groups, acyl-, acylamino or sulfonyl groups as well as halogen atoms. From the above mentioned groups which may be identical or different, several of them may be bound at the same time onto the naphthalene nuclei.

Functional derivatives of the carboxy group are firstly their salts with colorless cations, whereby alkali metal or eventually substituted ammonium ions are preferred; furthermore, the cyano group, the carboxylic acid ester group or the carboxylic acid amide group may especially be cited.

Carboxylic acid ester groups are especially those which correspond to the general formula $COOR^1$, in which $R^1$ stands for a phenyl radical or eventually for a branched lower alkyl group, whereby these radicals may contain further substituents such as preferably a low-molecular dialkylamino-, trialkylammonium- or alkoxy group. A carboxylic acid amide group is especially a group corresponding to the formula $CONR^2R^3$ in which the radicals $R^2$ and $R^3$ represent lower hydrogen atoms, or, eventually, substituted alkyl groups which may form together with the nitrogen atom a hydroaromatic ring system, furthermore carboxylic acid-hydrazides of the formula $CONHNR^2R^3$ in which $R^2$ and $R^3$ have the abovementioned meaning and in which the oxygen atom of the carboxy groups may be substituted entirely or partially by sulphur.

A functional derivative of the sulfo group, in analogy to the beforementioned explantions, is the salt with colorless cations, preferably with alkali metal- or eventually substituted ammonium-ions; furthermore, such derivatives are concerned in which the $SO_2$-group is bound to an hetero-atom, such as the sulfonic acid ester group and in the sulfonamide group. A sulfonic acid ester group is especially a group corresponding to the formula $SO_2OR^1$, in which $R^1$ has the above mentioned meaning and a sulfonic acid amide group of the formula $SO_2NR^2R^3$ in which $R^2$ and $R^3$ have the above mentioned meanings.

The acyl group corresponds to the formula $COR^4$ in which $R^4$ stands for an optionally substituted, preferably lower alkyl- or phenyl radical.

The sulfonyl radical is especially $SO_2R^5$ in which $R^5$ stands for an optionally substituted lower alkyl- or phenyl group, whereby these groups may contain as substituents preferably a lower dialkylamino-, trialkylammonium-, acylamino- or sulfo group.

Amongst the compounds of the general formula (1) those which correspond to the general formula (2) are especially valuable, in which X and $X^1$, which may be identical or different, have the meaning indicated in the formula (1),

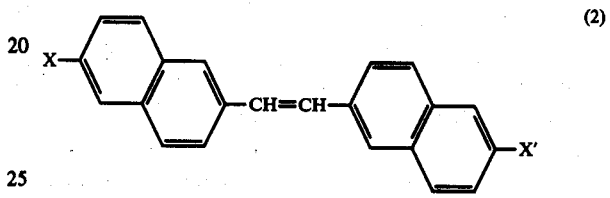 (2)

Preference is given to X and X' for cyano, carboxy or lower carboalkoxy group in which the alcohol radical may be substituted by dialkylamino- or lower trialkylammonium groups.

As far as aliphatic groups are earmarked as "low molecular, low-alkyles" or if similar groups are concerned, radicals with up to 4 carbon atoms are considered. If ionic substituents are present it is a rule that the compensating ion has to be colorless and should either not fluoresce, or fluoresce only in the same range as the basic molecule. Suitable cations are already mentioned under Me; suitable anions are halogenides, especially chloride, lower alkylsulfates, especially methosulfate, lower alkylsulfonates such as methylsulfonate and tosylate.

The compounds of the invention may be synthetized according to a process of preparation described hereafter, whereby the radicals X and X' have the meaning as indicated in formula (1), the radicals R stand for identical or different alkyl, cycloalkyl or phenyl radicals which are eventually bound by the means of a hydrogen atom onto the phosphorus atom and whereby the naphthalene nuclei may eventually contain further colorless substituents. As the radicals R are not incorporated in the end-product, their state is not critical in this respect. For R preference is given for reasons of easy accessibility to lower alkyl, especially to methyl and ethyl groups, to cycloalkyl radicals with 4 to 8 carbon atoms, especially cyclohexyl or phenyl groups.

The process is characterized thereby that phosphonomethyl naphthalenes of the general formula (3)

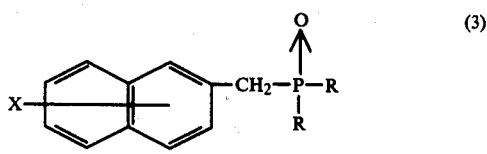 (3)

are condensed with substituted naphthaldehydes of the general formula (4)

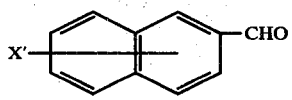
(4)

in inert organic solvents in the presence of alkaline condensation agents.

The process is preferably carried out in inert solvents, for example hydrocarbons such as toluene or xylene, or alcohols such as methanol, ethanol, isopropanol, butanol, glycol, ethers such as diisopropyl ether, methyl- respectively ethyl glycol, dioxane, tetrahydrofurane, furthermore in formamide or N-methyl-pyrrolidone. Particularly suitable are bipolar organic solvents such as dimethylformamide and dimethylsulfoxide.

As condensing agents there are considered strongly basic compounds, such as alkali or alkaline earth metal hydroxides, alkali or alkaline earth metal alcoholates or amides, preferably potassium hydroxide, sodium hydroxide, potassium-tert.-butylate or sodium methylate, furthermore the alkali metal compounds of the dimethyl sulfoxide and alkali hydrides.

Depending on the type of the starting materials, the reaction temperature ranges between about 0° and about 100° C., preferably between about 10° and 80° C.

For preparing the compounds according to the invention, the following phosphonomethyl naphthalenes of the general formula (3) are for example suitable

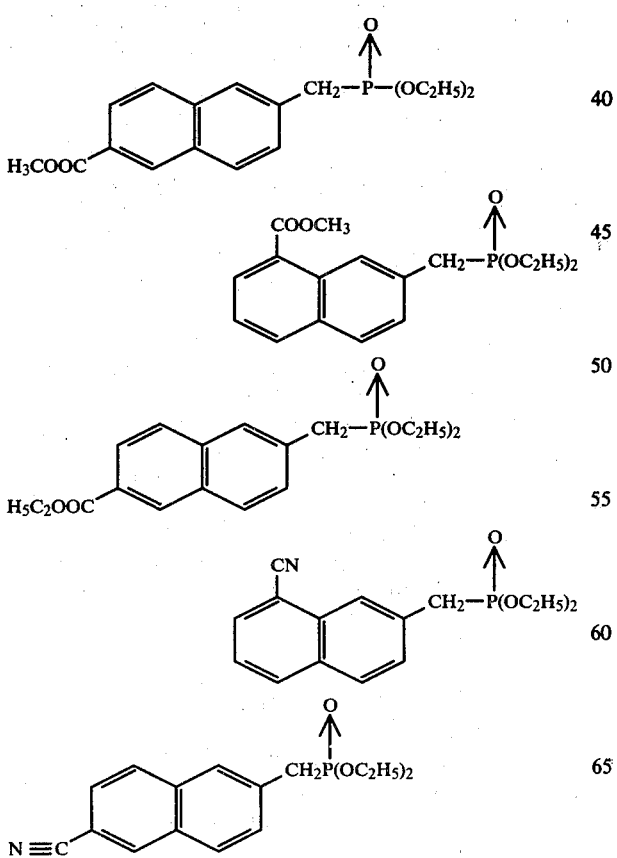

As substituted naphthaledehydes corresponding to the general formula (4) the following ones may for example be used.

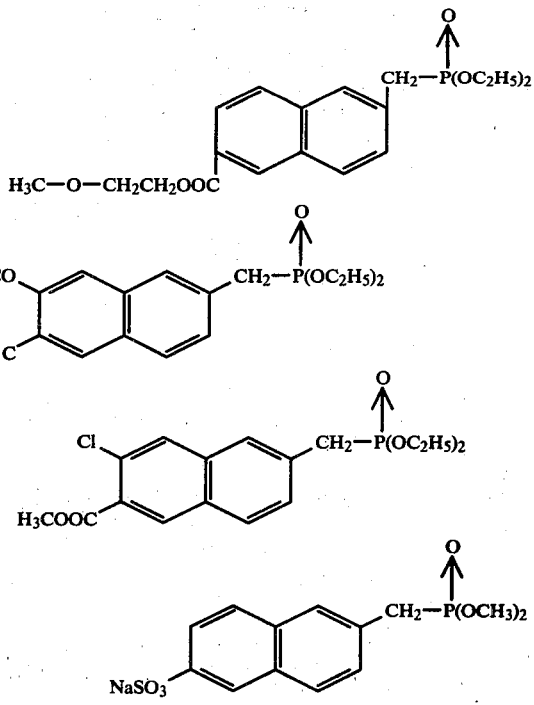

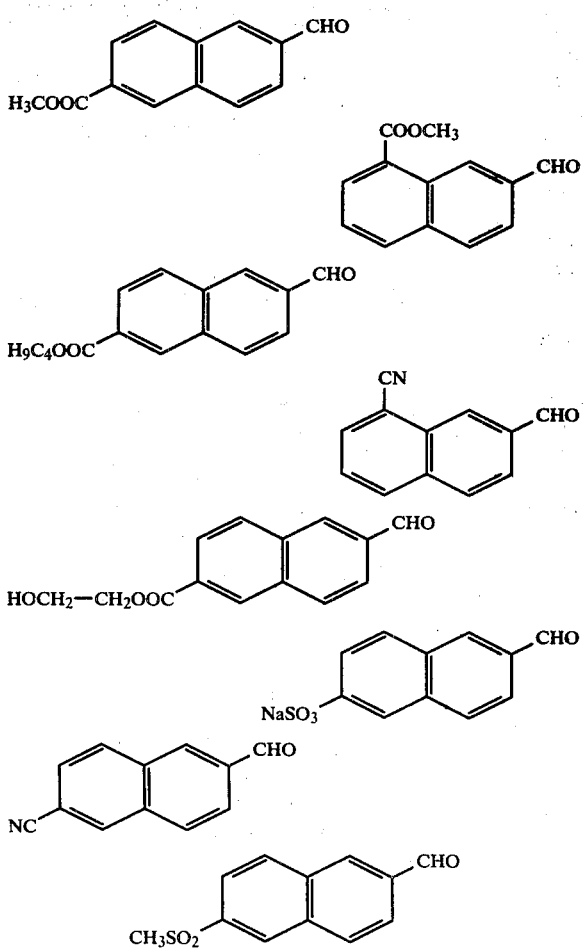

-continued

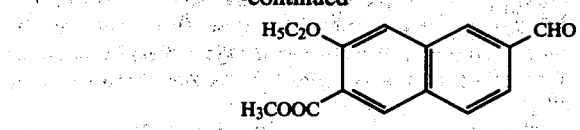

The reaction products of the beforementioned process may be submitted to generally known conversions, which — starting for example from molecules containing carboxy groups — lead to compounds having functional derivatives of carboxy groups, respectively to conversions of such groups into other groups of the same kind or into the free acids or their salts. Furthermore, sulfo groups may be incorporated be usual methods in the reaction product of the beforementioned process as well as sulfonamide radicals or chloromethyl groups; methyl groups can be oxidized in the same way. It is furthermore known that halogenations and further conversions of the introduced halogen atoms are successfully practiced such as, for example, the exchange of chloride or bromine by of the —C≡N— groups. The compounds according to the invention present, due to their fluorescenting capacity a broad field of application. First of all they can be used and are suitable for the optical brightening of different synthetic and natural organic, high molecular materials.

Synthetic organic, high molecular materials are polymerisation-, polycondensation- and polyaddition-products as well as the after-treatment products, for example, polymerisates based on $\alpha$, $\beta$-unsaturated carbonic acids, dicarbonic acids, carbonic acid esters, -amides, -nitriles, olefinehydrocarbons, halogenated or aryl groups containing olefine-hydrocarbons (such as polyethylene, polypropylene, polybutadiene, polyvinylchloride, polyvinylidenchloride, polyacrylnitrile, polystryrol, polyacrylic acid derivatives and copolymerisates from two or more above mentioned monomers, capable to polymerise), polycondensates based on bi- or polyfunctional compounds with groups capable to condensate, their homo- and co- condensation products (such as polyester, polyamide, maleinic resins, polycarbonates, silicon resins, phenol- and melamine formaldehyde resins and others), polyaddition products such as, for example, cross- or non cross-linked polyurethanes as well as epoxide resins.

Semi-synthetic organic materials are, for example, cellulosic esters and ethers, nitrocellulose, regenerated cellulose and synthetics based on caseine.

Natural, high molecular organic materials which can be brightened are for example, protein materials such as, cotton, paper, wood masses finely dispersed; furthermore caoutchouc, guttapercha or balata.

The organic materials to be brightened may be used in their different stages of manufacture as raw materials, semimanufacture or finished products, for example, as powder, chips, granulates, plastic foames; lacquers and varnishes, dispersions; shaped articles such as for example, foils, plates, films ribbons, filaments, fibres, for example in form of threads, fibre fleeces, felts, wads, textile fabrics, plastic steels and knitted fabrics; furthermore putties, pastes, waxes, adhesive- and putty coat masses etc.

The new optical brighteners may of course also be applied where organic materials of the abovementioned kind are combined in any form with inorganic materials.

The compounds of the invention are preferably used for optical brightening of fibre materials and synthetics. Especially suitable for the optical brightening of native and regenerated cellulosic fibres, or wool and synthetic polyamide fibres are the compounds of the invention which are anionic and soluble in water.

The cationic water-soluble compounds according to the invention, suit especially the optical brightening of homo- and copolymerisates of the acrylnitrile, specially the commercialized copolymers with a minimum content of about 85% of acrylnitrile units.

Insoluble compounds in water which suit especially the optical brightening of polyester- and polyamide fibres as well as regenerated cellulosic fibres and furthermore cellulose regenerated fibres, solely, or in a mixture with synthetic fibres, may be used in dissolved form in organic solvents or in an aqueous dispersion, preferably by means of a dispersing agent. As dispersing agents there may be used for example, soaps, polyglycol ethers of fatty alcohols, of fatty amines or alkyl phenols; cellulose sulfite waste liquors or condensation products of optionally alkylated naphthalene sulfonic acids with formaldehyde.

The compounds of the invention excell especially thereby, that they can be used in the presence of oxidative and reductive bleaching agents without prejudizing the effect of the optical brightening. In order to obtain a better effect or in order to simplify the process, the optical brighteners can be combined with other accessory agents. Such accessories are, for example retarders, carriers, dispersing agents, softeners, oleophobic or hydrophobic compounds, preparation agents, emulsifiers, detergents and wetting agents. Furthermore, the brightened fibre material, especially the polyester of the type "polyethyleneglycolteraphthalate" present an excellent fastness to light. High - brilliant, red to greenish brightening effects with extraordinarily high degrees of whiteness are obtained.

Especially good brightening effects are sometimes also obtained by combining the compounds of the invention with other optical brighteners. Such combinatons are of special interest if a shifting of the hue of the brightening effect in desired.

The brightening of the fibre material with aqueous or eventually organic baths containing the brightener is effected either by the exhaustion method at temperatures optionally between about 60° to 150° C. or under thermosoling conditions, whereby the textile material together with the brighteningsolution or dispersion is brought to a humidity content of about 50–120%, by impregnation and squeezing or by sprinkling. Afterwards, the textile material is submitted during about 10 to about 300 seconds to a temperature-treatment, preferably by dry heat at about 120° to about 240° C. This thermosoling process may also be combined with other finishing processes, for example, the finishing with artificial resins for a better maintenance. The brighteners according to the invention excell by their high resistance against the usual catalysts or additives such as magnesium chloride, or zinc nitrate but also against polyethylene dispersions.

Detergents may be added to the compounds of the general formula (1) of the invention. They may contain the usual filling materials and auxiliaries such as alkalinsilicates, phosphates and polymetaphosphates, alkali borates alkali salts of carboxymethyl cellulose, foam stabilisators such as alkanolamides of higher fatty acids or complexing agents such as so soluble salts of the ethylene diamintetra acetic acid or of the diethylentriaminepenta acetic acid as well as chemical bleaching agents such as perborates or percarbonates. Very good yields are also obtained with perborate containing detergents in the presence of perborate-activators. Furthermore, the usual desinfection agents used in detergents do not influence the brightening effect of the new compounds.

Furthermore, the compounds of the invention may be added to high-molecular organic materials before or during their transformation. It is for example possible to add these compounds to the synthetic powders, thermoplastic masses, molten masses, polymer-solutions or -dispersions when fibres, films, foils, ribbons, plates or other shaped materials are manufactured, for example, before the Spinning process in the spinning mass. Suitable compounds may also be added to the low-molecular starting materials before the polycondensation or polymerisation as in the case of polyamide -6.6 polyamide -6 or linear polyesters of the type "polyethyleneglycoltherephthalate."

Compounds of the invention which may be substituted by one or optionnally by two reactive groups such as carboxy groups, may be bound to linear polyester molecules and synthetic polyamides by an ester or amide link, if they are added to these materials or preferably to their starting materials under adequate conditions. In this way, brighteners bound chemically in the substrate, excell by an extraordinary high fastness to sublimation and to solvents.

In the last mentioned process, compounds of the invention having two carboxylic acid ester groups, may be used preferably in mixture with compounds of the formula (5)

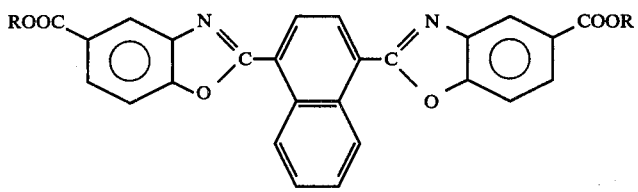

(5)

in which R stands for a lower or optionally substituted aliphatic alcohol especially for a methyl, ethyl or a β-hydroxyethyl group. In this way excellent whiteness degrees with very good fastnesses to light, sublimation and solvent are obtained. It is also possible to adjust the shade of the optically brightened synthetic fibres by varying the ratio of the mixture of suitable compounds of the invention with the compounds of the formula (5); therewith the requirements of the market in respect of the whiteness degree can be satisfied.

Olefine-unsaturated compounds of the invention which contain in addition to the fluorescenting system at least a further polymerisable olefinic double bond may be used for the preparation of fluorescent polymers or polymer-mixtures by polymerizing or engrafting them as such or in the mixture with other monomeric or polymeric vinyl compounds under maintainance of the fluorescent system. These fluorescent polymers may afterwards be mixed with non-fluorescent polymers. Such optically brightened polymers excell by a high degree of whiteness. Furthermore, a high fastness to sublimation and to solvents is granted due to the chemical link which exists between the brightening molecules and the polymers.

The amount of the new compounds corresponding to the general formula (1) brought in relation to the material to be optically brightened, may widely vary following the field or application and the requested effect. The amount of the compounds may easily be obtained by simple preliminary tests and ranges generally between about 0.01 and about 2%, preferably between 0.02 –0.1%.

The following examples illustrate the invention; the temperatures are expressed in centigrades (Celsius), percentages are percentages by weight and parts are parts by weight unless otherwise stated.

EXAMPLE 1

66.7 g of 6-bromomethyl-2-naphthonitrile (92%) were refluxed together with 114 ml of triethylphosphite and 400 ml of xylene during 4 hours. The solvents and the triethylphos phite in excess were distilled off under vacuum. 97 g of the so prepared phosphonic acid diethyl ester and 56.1 g of 6-formyl-2-naphtho acetic ethyl ester (97%) were dissolved in 200 ml of dimethylformamide (after wards quoted as DMF) and added to a suspension of 38 g of sodium ethylate in 250 ml of DMF at 25°–50° C. After half an hour the reaction mixture was stirred into 2.5 l of water. The precipitated product was suction-filtered, washed and dried. 82.8 g of the paleyellow raw-product were obtained (melting point: 187°–275° C.). The carboxylic acid formed during the condensation by saponification remained undissolved when poured into 1 l of o-dichlorobenzene. After cooling, yellowish crystals of the ethyl ester (compound nr. 14, se table I) were obtained. They were prepared in pure form by a further recrystallization from toluene by adding bleaching-earth.

The compounds nr. 10 to 13, listed in table I, were obtained in an analog process.

Table I

| Nr. | X | X' | Schmp. |
|---|---|---|---|
| 10 | —COOCH$_3$ | —COOCH$_3$ | 295 bis 296° |
| 11 | —COOC$_2$H$_5$ | —COOC$_2$H$_5$ | 209 bis 228° |
| 12 | —CN | —CN | 306 bis 309° |
| 13 | —CN | —COOCH$_3$ | 200 bis 205° |
| 14 | —CN | —COOC$_2$H$_5$ | 205 bis 206° |
| 15 | —CN | —COOH | >340° |
| 16 | —COOH | —COOH | >340° |
| 17 | —COOR$^6$ | —COOR$^6$ | 110 bis 113° |
| 18 | —COOR$^7$ | —COOR$^7$ | 192 bis 201° |
| 19 | —CN | —COOR$^6$ | 154 bis 156° |
| 20 | —CN | —COOR$^7$ | 218 bis 261° |

R$^6$: —CH$_2$—CH$_2$—N(C$_2$H$_5$)$_2$

R$^7$: —CH$_2$—CH$_2$—N$^\oplus$(CH$_3$)(C$_2$H$_5$)(C$_2$H$_5$)  $^\ominus$OSO$_3$CH$_3$ When condensating components containing carboxy-alic acid alkyl ester groups it is suggested to use the corresponding alkali alylates as condensing agent. In the case of nitriles, for example, compound nr. 12, alkali hydroxides can successfully be utilized.

The t-bromomethyl-2-naphthoic acid derivatives were prepared with the aid of 6-methyl-2-naphthoic acid derivatives by side chain bromination with N-bromo-succinimide.

Melting point of the starting materials

| Kind of the Substituent X | 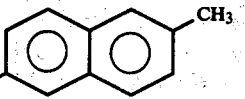 | 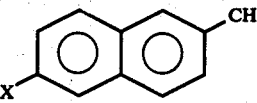 | 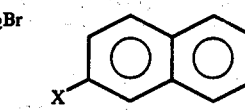 |
|---|---|---|---|
| CN | 126°–128° | 136°–137° | 178°–180° |
| COOCH$_3$ | 126°–127° | 102°–103° | 128°–129° |
| COOC$_2$H$_5$ | 56° | 98 – 99° | 85 – 86° |

The 6-formyl-2-naphthoic acid derivatives may be obtained either directly from the 6-methyl-2-naphthoic acid derivatives by catalytic oxidation or from the 6-bromomethyl-2-naphthoic acid derivatives by the SOMMELET reaction (hexamethylene tetramine).

EXAMPLE 2

34 g of the compound nr. 14 were dissolved in 400 ml of dioxane and boiled during 3 hours with a solution 6 g of sodium-hydroxide in 10 g of water.

By the addition of 16 ml of concentrated hydrochloric acid the carboxylic acid was precipitated. After addition of water the product was suction - filtered, washed and dried. 27.7 g of the compound no. 15 were obtained in form of a yellow powder.

EXAMPLE 3

34.9 g of the compound no. 15 were converted in 300 ml of chlorobenzene with 12.8 ml of thionyl chloride at 75°–125° to the acid chloride. The thionyl chloride in excess was taken off and 13.0 g of β- diethyl-aminoe-thanol were added. The crystalline mass of the hydrochloride was obtained after a rest of 15 hours by suction- filtering, was washed with cyclohexan and dried. By stirring it with a sodium bicarbonate solution the compound no. 19 was obtained.

Therefrom, the water- soluble quaternary salt (compound no. 20) was obtained by reaction with dimethyl-sulfate in dioxane.

EXAMPLE 4:

12 parts of dimethylerephthalate, 8 parts of ethylene-glycol and 0.025% of the compound no. 10 (table I) were melted in a rost proofed steel vessel with stirrer under an atmosphere of nitrogen at 140°–150°. When the molten mass had reached 145°, 0.02 parts of manganese acetate in one part of glycol were added at a temperature varying between 160°–220° the reesterification was effected within 3 hours under atmospheric pressure whereby methanol and, at the end of the reaction also glycol was partially distilled off.

The so obtained bis-(β-hydroxyethyl)-terephthalate was heated up to 240° in a rost proofed polycondensation vessel of steel after addition of 1 part of ethylene-glycol with 0.03% of antimonytrioxide
0.40% of titandioxide
0.031% of triphenylphosphite;

when this temperature was reached the pressure in the reaction vessel was slowly reduced to 0.4 Torr; at the same time the temperature was brought from 240° to 278°. The polycondensation is completed after 4 hours. Afterwards the vacuum was brought to nought and the free reaction space above the molten mass was filled with pressurized nitrogen. Afterwards the molten mass was pressed out by the nitrogen pressure and after cooling in water it was granulated and dried.

The so obtained product had a softening point of about 260° and an internal viscosity of about 600. The product is then spun in the usual way to filaments which are used for the production of weaved hoses.

In this way a material was obtained which had considerably higher whiteness degrees as that which was prepared without the compound No. 10.

Similar good results were obtained in cases where the compounds Nos. 11, 13, 14 and 16 were used instead of compound No. 10.

EXAMPLE 5

12 parts of dimethylterephthalate and 8 parts of ethylenglycol were melted in a rost proofed steel vessel with stirrer under an atmosphere of nitrogen at 140°–150°.

0.02 Parts of zinc acetate in 1 part of glycol were added to the molten mass heated up to 145°. At a temperature varying between 160°–220°, the conversion is effected within 3 hours and atmospheric pressure whereby methanol and, at the end of the reaction, also glycol was partially distilled off.

The so obtained bis-(β-hydroxyethyl)-terephthalate is pressed into a polycondensation vessel of rost proofed steel. After addition of 1 part of ethyleneglycol with 0.03% of antimonytrioxide
0.40% of titandioxide
0.031% of triphenylphosphite
0.025% of the compound no. 13 the temperature of the molten mass was brought up to 240°. When this temperature was reached the pressure in the reaction vessel was slowly reduced to 0.4 Torr; at the same time the temperature was brought to 278°. The polycondensation is completed after 4 hours. The vacuum is brought to nought and the free reaction space above the molten mass was filled with pressurized nitrogen. Afterwards, the molten mass was pressed out by the nitrogen pressure and after cooling in water it was granulated and dried.

The so obtained product had an internal viscosity of about 600 and a softening point of about 260°.

The granulate is then spun in the usual way to threads which are used for the production of weaved hoses.

In this way a material was obtained which had considerably higher whiteness degrees as that which was prepared without compound no. 13.

Similar good results were obtained in cases where the compounds no. 10, 11, 14 and 15 were used instead of compound No. 13.

EXAMPLE 6

In the same way as described in example 4, a mixture of 0.015% of the compound no. 10 and 0.010% of the compound of the formula (5), R = methyl, were used for the polycondensation. Very brilliant white-shades with a somewhat greenish hul were obtained.

EXAMPLE 7

0.03 Parts of the compound no. 18 were homogenously distributed by stirring in 75 parts of polyvinylchloride powder
25 parts of dioctylphthalate
1.5 parts of barium - cadmium stabilisator
2 parts of titandioxide and
0.2 parts of montanacid glycol ester wax.

The mass is then plastified between heated, polished steel cylinders at 160° during 10 minutes and then rolled to a foil of 0.5 mm.

The so obtained foil presented against foils in which compound no. 13 was not used considerably increased whiteness-degrees. In comparison with non-brightened material, the same whiteness- degree increases were obtained with the compounds Nos. 14 and 10.

EXAMPLE 8

Onto 98.5 g of polystyrolgranulate 1.5 g of titandioxide and
0.03 g of the compound No. 10 are homogenously applied in powdered form in an rotating vessel.

The so obtained material served to prepare small plates of a strength of 2 mm.

The plates so prepared and containing the compound No. 10 have in comparison with non-brightened materials a considerably better whiteness-degree. Compared with non brightened material, also compound No. 11 provides considerably increased whiteness-degrees.

EXAMPLE 9

A fabric of polyethyleneglycol terephthalate was impregnated in an aqueous bath which contained in dispersed form 1g/l of the compound No. 14. The so treated textile material was squeezed by cylinders until it contained only 80% of liquid of its dry- weight; afterwards a hot - air treatment at 160° followed. After this treatment the fabric presented an excellent whiteness degree. Similar good results were obtained with compounds Nos. 13 and 11.

EXAMPLE 10

In a conventional dyeing apparatus a yarn of polyethylenglycol-terephthalate was treated with an aqueous bath containing 0.1% (compared with the weight of the material) of the compound No. 13 in dispersed form. The bath of a temperature of 60° was heated within 30 minutes together with the fabric up to 120° and kept at this temperature during 30 minutes. After the cooling of the bath the goods were carefully rinsed and dried. The yarn presented, compared with the raw material, after the treatment a very high degree of whiteness. Compounds No. 14 and 11 could be used in a similar advantageous way.

EXAMPLE 11

A fabric of polyethylenglycol terephthalate was impregnated with a perchloroethylene solution in which 1g/l of the compound No. 12 or 14 was dissolved. The so treated textile material was squeezed by cylinders until it contained only 80% of liquid. Afterwards a hot-air treatment at 180° followed during 30 seconds. The fabric presented after this treatment an excellent degree of whiteness.

EXAMPLE 12

A fabric of polyamide - 6 was treated in a bath, ratio 1 : 20, which contained in dispersed form 0.20% of an optical brightener of the formula No. 14 or 13. The pH value of the bath was adjusted to 4 with the aid of oxalic acid. The bath was then slowly heated to boiling temperature and the substrate was treated therein during 30 minutes. Afterwards the goods were rinsed and finished in the usual way. In comparison with the raw- products, a high improvement of the whiteness-degree was obtained.

I claim:
1. A compound of the formula

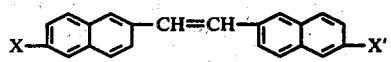

wherein X and X' which may be the same or different are cyano, carboxylic acid, carboxylic acid lower alkyl ester, carboxylic acid di lower alkylamino alkyl ester or carboxylic acid tri lower alkyl ammonium alkyl ester.

2. A compound of the formula

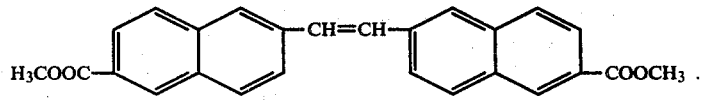

* * * * *